United States Patent
Barberousse et al.

(10) Patent No.: US 6,927,209 B2
(45) Date of Patent: Aug. 9, 2005

(54) 5-THIO-β-D-XYLOPRYANOSIDE DERIVATIVES, PREPARATION, METHOD, PHARMACEUTICAL COMPOSITIONS CONTAINING THEM AND THEIR THERAPEUTIC USE

(75) Inventors: Véronique Barberousse, Hauteville-les-Dijon (FR); Soth Samreth, Daix (FR)

(73) Assignee: Laboratoires Fournier S.A., Dijon (FR)

( * ) Notice: Subject to any disclaimer, the term of this patent is extended or adjusted under 35 U.S.C. 154(b) by 135 days.

(21) Appl. No.: 10/139,908

(22) Filed: May 6, 2002

(65) Prior Publication Data

US 2002/0198193 A1 Dec. 26, 2002

(30) Foreign Application Priority Data

May 11, 2001 (FR) .............................. 01 06236

(51) Int. Cl.$^7$ ................... A61K 31/55; A61K 31/5377; A61K 31/496
(52) U.S. Cl. ................ 514/27; 514/25; 514/217.03; 514/231.5; 514/252.13; 536/4.1; 536/18.1; 536/122; 540/596; 549/13
(58) Field of Search ............... 514/24, 25, 27, 514/231.5, 252.13, 217.03; 540/596; 549/13; 536/4.1, 18.1, 122, 18.2

(56) References Cited

U.S. PATENT DOCUMENTS 5,169,838 A 12/1992 Samreth et al.

FOREIGN PATENT DOCUMENTS

EP 0 421 829 4/1991

OTHER PUBLICATIONS

Organic Syntheses, Collective vol. 5, 1973, pp. 1–5.*
Carey et al, Advanced Organic Chemistry, Part B, 3$^{rd}$ edition, 1990, p. 151.*

* cited by examiner

Primary Examiner—James O. Wilson
Assistant Examiner—Ganapathy Krishnan
(74) Attorney, Agent, or Firm—Merchant & Gould P.C.

(57) ABSTRACT

The present invention relates to novel compounds of formula (I):

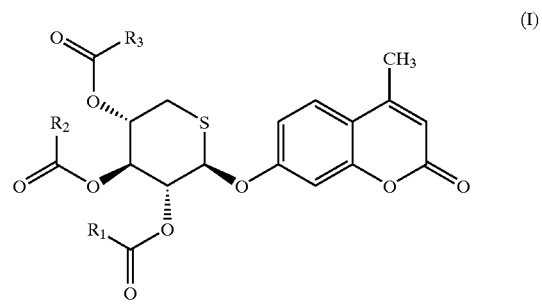

in which:

$R_1$, $R_2$ and $R_3$, which are identical or different, are each independently:

a ($C_1$–$C_6$)alkyl group, a pyridinyl group or a group —$CH_2$—$NR_4R_5$, in which $R_4$ and $R_5$ are each independently a hydrogen atom or a ($C_1$–$C_4$)alkyl group, or alternatively $R_4$ and $R_5$ form, with the nitrogen atom to which they are bonded, a pyrrolidinyl, piperidinyl, hexahydroazepinyl, morpholinyl or piperazinyl group, with the proviso that at least one of the substituents $R_1$, $R_2$ and $R_3$ is other than a ($C_1$–$C_6$)alkyl group, and their salts, solvates and hydrates, especially those which are pharmaceutically acceptable.

These compounds are useful particularly for the treatment of disorders of the venous circulation.

7 Claims, No Drawings

5-THIO-β-D-XYLOPRYANOSIDE DERIVATIVES, PREPARATION, METHOD, PHARMACEUTICAL COMPOSITIONS CONTAINING THEM AND THEIR THERAPEUTIC USE

The present invention relates to novel 4-methyl-2-oxo-2H-1-benzopyran-7-yl 5-thio-β-D-xylopyranoside derivatives, to their use for the preparation of antithrombotic drugs and to the pharmaceutical compositions containing them. The invention further relates to a method for the preparation of these compounds.

Patent EP 421 829 describes benzopyranone β-D-thioxylosides of formula (A):

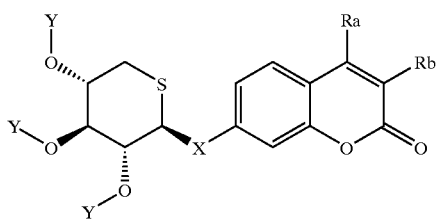

(A)

in which:
X is O or S,
Y is especially a hydrogen atom or the group —COCH$_3$,
Ra is especially a (C$_1$–C$_4$)alkyl group and
Rb is in particular a hydrogen atom, a (C$_1$–C$_4$)alkyl group or a halogen atom.

These compounds are useful in the treatment and prevention of diseases associated with circulatory disorders, especially as venous antithrombotics.

However, the compounds described in EP 421 829 are insufficiently soluble, especially in physiologically acceptable solvents, to allow them to be administered by injection. Thus they cannot be used in cases of emergency administration or on unconscious patients for whom injection is the only possible route of administration, or if it is preferable for the sake of convenience to administer one of these compounds in association with other drugs by perfusion.

The present invention relates to novel 4-methyl-2-oxo-2H-1-benzopyran-7-yl 5-thio-β-D-xylopyranoside derivatives with an antithrombotic activity. These compounds have a good solubility in the conventional physiologically acceptable solvents, especially injectable solutions. They can therefore be administered both orally and by injection, especially intravenous injection.

According to one of its features, the invention therefore relates to the compounds of formula (I):

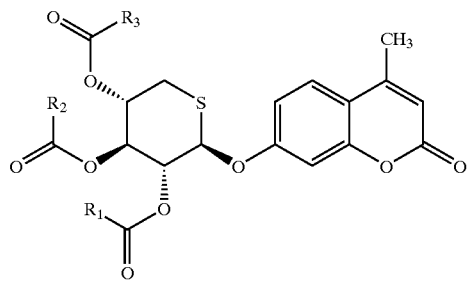

(I)

in which:
R$_1$, R$_2$ and R$_3$, which are identical or different, are each independently:

a (C$_1$–C$_6$)alkyl group, a pyridinyl group or a group —CH$_2$—NR$_4$R$_5$ in which R$_4$ and R$_5$ are each independently a hydrogen atom or a (C$_1$–C$_4$)alkyl group, or alternatively R$_4$ and R$_5$ form, with the nitrogen atom to which they are bonded, a pyrrolidinyl, piperidinyl, hexahydroazepinyl, morpholinyl or piperazinyl group, with the proviso that at least one of the substituents R$_1$, R$_2$ and R$_3$ is other than a (C$_1$–C$_6$)alkyl group, and their salts, solvates and hydrates, especially those which are pharmaceutically acceptable.

In the present description, (C$_1$–C$_4$)alkyl group is understood as meaning a linear or branched, saturated hydrocarbon chain having from 1 to 4 carbon atoms. Examples of (C$_1$–C$_4$)alkyl groups include methyl, ethyl, propyl, butyl, 1-methylethyl, 1-methylpropyl, 2-methylpropyl and 1,1-dimethylethyl groups. (C$_1$–C$_6$)alkyl group is understood as meaning a linear or branched, saturated hydrocarbon chain having from 1 to 6 carbon atoms. Examples of (C$_1$–C$_6$)alkyl groups include those listed above and also pentyl and hexyl groups.

Salts are understood as meaning the addition salts obtained by reacting a compound of formula I, containing at least one basic functional group in its non-salified form, with a mineral or organic acid. Said addition salts will preferably be those which are pharmaceutically acceptable.

Hydrochloric, hydrobromic, phosphoric and sulfuric acids are preferred among the mineral acids which are suitable for salifying a basic compound of formula I. Methanesulfonic and trifluoroacetic acids are preferred among the organic acids which are suitable for salifying a basic compound of formula I.

The preferred compounds of formula (I) of the invention are those in which:
R$_1$, R$_2$ and R$_3$, which are identical or different, are each independently:

a (C$_1$–C$_4$)alkyl group, a pyridin-3-yl group or a group —CH$_2$—NR$_4$R$_5$ in which R$_4$ and R$_5$ are each independently a hydrogen atom or a (C$_1$–C$_4$)alkyl group, or alternatively R$_4$ and R$_5$ form, with the nitrogen atom to which they are bonded, a pyrrolidinyl, piperidinyl or morpholinyl group, with the proviso that at least one of the substituents R$_1$, R$_2$ and R$_3$ is other than a (C$_1$–C$_4$)alkyl group, and their pharmaceutically acceptable salts, solvates and hydrates.

The compounds of formula (I) in which at least two of the substituents R$_1$, R$_2$ and R$_3$ are identical, and their pharmaceutically acceptable salts, solvates and hydrates, are also preferred compounds of the invention.

The compounds of formula (I) in which R$_1$, R$_2$ and R$_3$ are identical, and their pharmaceutically acceptable salts, solvates and hydrates, are also preferred compounds of the invention.

According to another feature, the invention relates to a method for the preparation of the compounds of formula (I) which comprises the steps consisting in:

1) reacting a 5-thio-β-D-xylopyranoside derivative of formula (II):

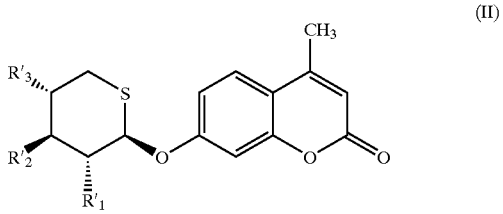

in which:
either R'$_1$, R'$_2$ and R'$_3$ are identical and are a hydroxyl group,
or two of the substituents R'$_1$, R'$_2$ and R'$_3$ are identical and are a hydroxyl group and the other substituent R'$_1$, R'$_2$ or R'$_3$ is respectively —OC(O)R$_1$, —OC(O)R$_2$ or —OC(O)R$_3$, where R$_1$, R$_2$ and R$_3$ are as defined for (I),
or one of the substituents R'$_1$, R'$_2$ and R'$_3$ is a hydroxyl group and the other two substituents R'$_1$, R'$_2$ and R'$_3$ are respectively —OC(O)R$_1$, —OC(O)R$_2$ or —OC(O)R$_3$, where R$_1$, R$_2$ and R$_3$ are as defined for (I),
with an appropriate acid of formula (III):

or an appropriate acid halide of formula (IIIa):

in which Hal is a halogen atom, especially chlorine, fluorine or bromine and preferably chlorine, and R is R$_1$, R$_2$ or R$_3$ as defined for (I); and 2) optionally converting the resulting compound of formula (I) to one of its salts.

The first step of the method of the invention is an esterification step, which can be carried out by the procedures well known to those skilled in the art.

Advantageously, this esterification step is carried out with the aid of a coupling agent such as a carbodiimide, for example 1-[3-(dimethylamino)propyl]-3-ethylcarbodiimide (EDCI), preferably in the presence of 1-hydroxybenzotriazole (HOBT).

The esterification reaction is generally carried out in an anhydrous solvent, for example dimethylformamide (DMF), pyridine or dichloromethane, in the presence of an aprotic base such as triethylamine, 4-dimethylaminopyridine (DMAP) or mixtures thereof.

The reaction is preferably carried out under a dry inert atmosphere, for example under a nitrogen or argon atmosphere, and in the presence of a moisture trap such as a molecular sieve.

The reaction is advantageously carried out between room temperature and the reflux temperature of the solvent.

The second step of the method of the invention is a salification step, which is carried out by methods well known to those skilled in the art, the compounds of formula (I) being reacted with mineral or organic acids, especially those which are pharmaceutically acceptable, for example hydrochloric acid, methanesulfonic acid or trifluoroacetic acid.

The acids (III) and acid halides (IIIa) are commercially available compounds or are prepared by conventional methods.

The compound of formula (II) in which R'$_1$=R'$_2$=R'$_3$=OH, hereafter called compound II.1, is described in patent EP421 829. The other compounds of formula (II) can be obtained from the compound II.1 by reaction with an acid or an acid halide of formula (III) or (IIIa), in which the groups R$_1$, R$_2$ and R$_3$ are optionally protected as indicated below.

The compounds of formula (II) can also be obtained from the stannylene-type derivative of formula (IV):

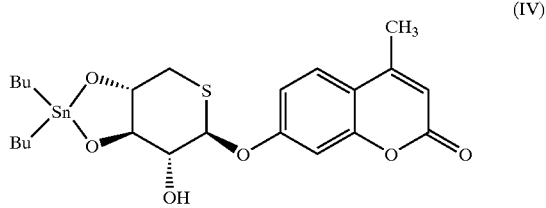

in which Bu denotes butyl, following the procedure described e.g. in *J. Org. Chem.* 1991,56,7015.

The ester-type functional groups of the compound (II) can be obtained selectively by reacting one or two equivalents of appropriate acylating agents of formula (IIIa) with the compound of formula (IV).

If the radicals R$_1$, R$_2$ and/or R$_3$ contain free amine groups, they are preferably protected with protecting groups so that the desired compounds of formula (I) can be obtained.

The protection and deprotection reactions are carried out by the techniques well known to those skilled in the art. The tert-butoxycarbonyl group, which is cleavable in an acid medium, will advantageously be used as the protecting group for the amine group.

In the remainder of the description, the compounds of formula (II) protected in this way will be called compounds (I'). They are obtained by reacting the compounds of formula (II) with an acid or an acid halide of formula (III) or (IIIa) in which the groups R$_1$, R$_2$ and R$_3$ are protected.

The compounds according to the invention were the subject of pharmacological studies.

The antithrombotic activity of the compounds according to the invention was studied in vivo in the rat by means of a test which reproduces venous thrombosis.

The oral activity was studied according to the protocol described in *Thromb. Haemost.* 1992, 67(1), 176–179. The intravenous or oral activity was studied according to the following operating protocol:

The experiments are performed on non-fasted Wistar male rats weighing 250 to 280 g, divided into groups of 10 animals each. The test products are administered either orally (tubage) dissolved or suspended in isotonic solution, or by intravenous injection dissolved in isotonic solution. The concentration of the compounds is calculated so that the amount of solution absorbed is 2 ml/kg by oral administration and 1 ml/kg by intravenous injection. Thrombosis is induced at a time T (2, 4 or 8 hours) after the administration of the product, and the thrombus formed is removed and weighed. To induce this thrombosis, a venous stasis is created under hypercoagulation according to the technique described by WESSLER (*J. Applied Physiol.* 1959, 943–946), the hypercoagulating agent used being a solution of activated factor X (Xa) having a concentration of 7.5 nKat/kg, supplied by Biogenic. The activity of the test compounds was checked at different doses after they had been administered either orally (p.o.) or intravenously (i.v.). The thrombosis was induced 4 hours or 8 hours after oral administration of the compound and 2 hours after intravenous administration of the compound. For doses varying between 8 and 17 mg p.o., the percentage inhibition obtained after 4 hours, calculated relative to the weight of a thrombus obtained in the absence of active principle in the isotonic solution, varied between 40 and 99%. For doses varying between 5 and 7 mg i.v., the percentage inhibition obtained after 2 hours varied between 40 and 95%.

These results show that the compounds according to the invention exhibit an antithrombotic activity, particularly on venous thrombosis, by both oral and intravenous administration.

By way of comparison, the compounds described in EP421 829 are insoluble in isotonic solution and cannot therefore be administered intravenously.

The present invention therefore relates to the compounds of formula (I) according to the invention, and their pharmaceutically acceptable salts, solvates and hydrates, for use as drugs. The compounds of formula (I), or one of their pharmaceutically acceptable salts, solvates or hydrates, may be used for the preparation of an antithrombotic drug intended in particular for the treatment or prevention of disorders of the venous circulation and especially for correcting certain hematological parameters perceptible in the venous system.

The present invention therefore further relates to pharmaceutical compositions containing a compound of formula (I) or one of its pharmaceutically acceptable salts, solvates or hydrates. These pharmaceutical compositions generally contain suitable excipients. Said excipients are chosen according to the desired pharmaceutical form and the desired mode of administration, particularly oral administration or administration by injection.

These pharmaceutical compositions are prepared by the conventional methods well known to those skilled in the art. For example, the compounds according to the invention can be formulated with physiologically acceptable excipients to give an injectable form for direct use, an injectable form to be prepared immediately before use, or a solid form for oral administration, for example a gelatin capsule or a tablet.

By way of example, an injectable form can preferably be prepared by the lyophilization of a sterilized filtered solution containing the compound according to the invention and a soluble excipient in a necessary and sufficient amount to give an isotonic solution after the addition of injectable water immediately before use. An oral form will preferably be presented in the form of a gelatin capsule containing the finely ground or, preferably, micronized compound of the invention mixed with excipients known to those skilled in the art, for example lactose, pregelatinized starch and magnesium stearate.

To obtain the desired therapeutic or prophylactic effect, each unit dose can contain 25 to 500 mg of at least one compound according to the invention.

In the Examples which follow, "preparation" denotes the Examples describing the synthesis of intermediates, and "Example" denotes those describing the synthesis of compounds of formula (I) according to the invention. These Examples are intended to illustrate the invention and cannot in any way limit its scope. The melting points are measured on a Koffler bench and the nuclear magnetic resonance spectral values are characterized by the chemical shift calculated relative to TMS, by the number of protons associated with the signal, and by the shape of the signal (s for singlet, d for doublet, t for triplet, q for quadruplet, m for multiplet). The operating frequency and the solvent used are indicated for each compound.

In these Examples, the abbreviation DMSO denotes dimethyl sulfoxide.

Preparation 1
N-Morpholinoacetic Acid, Compound III.1
a) Benzyl N-morpholinoacetate 3 ml of morpholine are added under a stream of argon at room temperature to a solution of 5.03 g of benzyl 2-bromoacetate in 75 ml of tetrahydrofuran. A white precipitate forms instantly. The mixture is then stirred for 17 hours. The white salt which has precipitated is filtered off and washed with 50 ml of ethyl acetate. The filtrate is washed successively with 50 ml of saturated aqueous sodium carbonate solution, 50 ml of water and 50 ml of saturated aqueous sodium chloride solution. The organic phase is dried over magnesium sulfate, filtered and evaporated and the residual yellow liquid is purified by chromatography on silica gel (eluent: ethyl acetate/hexane, 6/4, v/v). (Yield=64%)

b) N-Morpholinoacetic Acid 325 mg of palladium on activated charcoal are added to a solution of 3.25 g of benzyl N-morpholinoacetate in 100 ml of ethanol. The mixture is then stirred under a hydrogen atmosphere at room temperature for 17 hours. The catalyst is filtered off and rinsed with 2×50 ml of methanol. The filtrate is evaporated to give the expected product in the form of a white solid. (Yield=97%) M.p.=151–155° C.

The following compounds are synthesized in the same manner:
N-piperidinoacetic acid, compound III.2; m.p.=209–212° C.
N-pyrrolidinoacetic acid, compound III.3; m.p.=138–141° C.
N,N-diethylglycine, compound III.4; m.p.=131–133° C.

Preparation 2
4-Methyl-2-oxo-2H-1-benzopyran-7-yl 3,4-di-O-acetyl-5-thio-β-D-xylopyranoside, compound II.2
4-Methyl-2-oxo-2H-1-benzopyran-7-yl 2,4-di-O-acetyl-5-thio-β-D-xylopyranoside, compound II.3
a) 4-Methyl-2-oxo-2H-1-benzopyran-7-yl 3,4-di-O-(dibutylstannylene)-5-thio-β-D-xylopyranoside, compound IV A suspension of 4 g of 4-methyl-2-oxo-2H-1-benzopyran-7-yl 5-thio-β-D-xylopyranoside (compound II.1) and 6.14 g of dibutyltin oxide in 200 ml of methanol is stirred under reflux for 4 hours in a round-bottom flask equipped with a Soxhlet apparatus fitted with a cartridge containing a 4 Å molecular sieve. After filtration of the reaction mixture, the solvent is evaporated off under reduced pressure. The resulting compound IV is used as such in the next steps.

b) A solution of 1.9 g of acetyl chloride in 20 ml of dioxane is added dropwise to a suspension of 6.25 g of compound IV in 200 ml of dioxane. After 2 hours at 30° C., the reaction mixture is filtered and the solvents are evaporated off under reduced pressure. 1.5 g of compound II.2 (34%) and 660 mg of compound 11.3 (14%) are separated out by chromatography on silica gel (cyclohexane/ethyl acetate, 45/55, v/v).

Compound II.2: m.p.=169° C.; $[\alpha]_D^2=-162°$ (c=0.2, CHCl$_3$) Compound II.3: $^1$H NMR (300 MHz, DMSO): 7.70 (d, 1H); 7.17 (d, 1H); 7.00 (dd, 1H); 6.28 (s, 1H); 5.75 (d, 1H, J$_{12}$=9 Hz); 5.16 (t, 1H); 4.77 (m, 1H); 3.62 (m, 1H); 2.84 (m, 2H); 2.40 (s, 3H); 2.00 (s, 3H); 1.96 (s, 3H)

Preparation 3
4-Methyl-2-oxo-2H-1-benzopyran-7-yl 4-O-(2,2-dimethylpropanoyl)-5-thio-β-D-xylopyranoside, Compound II.4

19.575 g of trimethylacetyl chloride are added dropwise to a suspension of 41 g of compound IV obtained in PREPARATION 2 in 800 ml of dioxane. After 2 hours at 30° C., the reaction mixture is filtered. The filtrates are taken up in ethyl acetate, washed with water and then dried over magnesium sulfate. The solvents are evaporated off under reduced pressure and the residue obtained is purified by chromatography on a silica gel column (eluent: cyclohexane/ethyl acetate, 55/45, v/v). (Yield=59%)

M.p.=160° C.; $[\alpha]_D^{23}$=−97° (c=0.5, $CH_3OH$)

Preparation 4

4-Methyl-2-oxo-2H-1-benzopyran-7-yl 4-O-acetyl-5-thio-β-D-xylopyranoside, Compound II.5

0.57 ml of acetyl chloride is added under an inert atmosphere to a solution of 4.4 g of compound IV obtained in PREPARATION 2 in 20 ml of dichloromethane, a further 0.2 ml being added after stirring for 5 hours. The reaction mixture is stirred for 3 days. After filtration, the compound 11.5 is obtained. (Yield=61%)

M.p.=210° C.; $[\alpha]_D^{22}$=−68° (c=0.48, DMSO)

EXAMPLE 1

4-Methyl-2-oxo-2H-1-benzopyran-7-yl 2,3,4-tri-O-[(dimethylamino)acetyl]-5-thio-β-D-xylopyranoside 2 ml of triethylamine, 2.84 g of 1-[3-(dimethylamino)propyl]-3-ethylcarbodiimide (EDCI), 0.56 g of 4dimethylaminopyridine (DMAP), 30 ml of a 0.5 M solution of 1-hydroxybenzotriazole hydrate (HOBT) in DMF and 1.53 g of N,N-dimethylglycine are added successively under an argon atmosphere and in the presence of a 3 Å molecular sieve to a solution of 1 g of 4-methyl-2-oxo-2H-1-benzopyran-7-yl 5-thio-β-D-xylopyranoside (compound II.1) in 25 ml of dimethylformamide (DMF). The reaction mixture is then stirred for 18 hours. The precipitate is filtered off and rinsed with 30 ml of ethyl acetate. The filtrate is concentrated and the residual orange oil is taken up in 100 ml of water and 15 ml of triethylamine. The aqueous phase is extracted with ethyl acetate (100 ml+50 ml). The organic phases are combined and washed with 50 ml of water and then with 50 ml of saturated aqueous sodium chloride solution. The organic phase is then dried over magnesium sulfate, filtered and concentrated. The residual yellow solid is chromatographed on silica gel (eluent: ethyl acetate/triethylamine 99/1, v/v, then dichloromethane/methanol/triethylamine, 9/1/0.1, v/v/v). The fraction collected is evaporated and the residual yellowish solid foam is taken up in diethyl ether. The desired product is filtered off and rinsed with diethyl ether. (Yield=72%)

M.p.=112–114° C.

The corresponding trihydrochloride (EXAMPLE 1A) is prepared by adding 7.5 ml of a 1 M solution of hydrogen chloride in diethyl ether to a solution of 0.7 g of the compound of EXAMPLE 1 in 3 ml of anhydrous methanol at 0° C. A yellowish paste then forms instantly. The mixture is subsequently diluted with 5 ml of anhydrous diethyl ether, stirred at 0° C. for 1 hour and then concentrated to give a yellowish solid.

M.p.=196° C.; $[\alpha]_D^{29}$=−32° (c=0.55, $CH_3OH$)

EXAMPLES 2 to 5A shown in TABLE 1 below are prepared by following the same procedure starting from the corresponding acid (III), in the presence or absence of HOBT.

TABLE 1

(I)

| EXAMPLE | $R_1$ | M.p. (° C.) or $^1H$ NMR |
|---|---|---|
| 2 | —$CH_2$—N(piperidinyl) | M.p. = 209–212 |
| 2A | —$CH_2$—N(piperidinyl), HCl | M.p. = 194 |
| 3 | —$CH_2$—N(pyrrolidinyl) | M.p. = 51–55 |
| 3A | —$CH_2$—N(pyrrolidinyl), HCl | M.p. = 187 |
| 4 | —$CH_2$—N($CH_2CH_3$)$_2$ | $^1H$ NMR (300 MHz, $CDCl_3$): 7.50(d, 1H); 6.96(2d, 2H); 6.18 (s, 1H); 5.54(m, 1H); 5.24(m, 3H); 3.28(s, 4H); 3.24(s, 2H); 3.03(m, 1H); 2.58(m, 13H); 2.39 (s, 3H); 0.96(m, 8H) |
| 4A | —$CH_2$—N($CH_2CH_3$)$_2$.HCl | M.p. = 149 |
| 5 | —$CH_2$—N(morpholinyl) | M.p. = 215 |
| 5A | —$CH_2$—N(morpholinyl), HCl | M.p. = 198 |

EXAMPLE 6

4-Methyl-2-oxo-2H-1-benzopyran-7-yl 2,3,4-tri-O-(pyridin-3-ylcarbonyl)-5-thio-β-D-xylopyranoside 4 g of compound II.1 and 11 g of nicotinoyl chloride hydrochloride in 50 ml of pyridine are stirred at room temperature for 48 hours. The reaction mixture is filtered and the solvents are evaporated off. The residue obtained is washed with water and then purified by chromatography on silica gel using a dichloromethane/methanol/aqueous ammonia mixture, 95/5/0.5, v/v/v, as the eluent. The white powder obtained is dried under reduced pressure.

$[\alpha]_D^{26}$=37° (c=0.6, $CHCl_3$)

EXAMPLE 7

4-Methyl-2-oxo-2H-1-benzopyran-7-yl 3-O-[(dimethylamino)acetyl]-2,4-di-O-acetyl-5-thio-β-D-xylopyranoside A solution of 620 mg of compound II.3 in 20 ml of dichloromethane glib stabilized with amylene, in the presence of 563 mg of EDCI, 302 mg of N,N-dimethylglycine and 89 mg of DMAP, is refluxed for 1 hour. The reaction mixture is then filtered. The filtrate is washed with a solution of ammonium chloride and sodium chloride and the organic phase is then dried over magnesium sulfate. The solvents are evaporated off under reduced pressure and the residue obtained is purified by chromatography on silica gel (eluent: toluene/isopropanol, 10/1, v/v). (Yield=76%)

M.p.=214° C.

$^1$H NMR (300 MHz, DMSO): 6.00 (d, 1H, $J_{12}$=8.4 Hz); 5.32 (2t, 2H); 4.98 (m, 1H); 3.15 (m, 3H); 2.94 (m, 1H); 2.40 (s, 3H); 2.21 (s, 6H); 2.00 and 1.92 (2s, 6H)

The corresponding methanesulfonate (EXAMPLE 7A) is obtained as follows: 466 mg of the compound of EXAMPLE 7 are dissolved in 30 ml of ethyl acetate. A solution of 92 mg of methanesulfonic acid in 4 ml of tetrahydrofuran is added to this ethyl acetate solution. After one hour, the reaction mixture is filtered. (Yield=79%)

M.p.=203° C.; $[\alpha]_D^{21.5}$=−56° (c=0.44, CHCl$_3$)

EXAMPLE 8

4-Methyl-2-oxo-2H-1-benzopyran-7-yl 2-O-[(dimethylamino)acetyl]-3,4-di-O-acetyl-5-thio -β-D-xylopyranoside The compound of EXAMPLE 8 is prepared from the compound II.2 by a procedure analogous to that of EXAMPLE 7. (Yield=92%)

M.p.=102° C. $^1$H NMR (300 MHz, DMSO): 6.02 (d, 1H, $J_{12}$=8.9 Hz); 5.4 (t, 1H); 5.26 (t, 1H); 5.00 (m, 1H); 3.08 (m, 3H); 2.95 (m, 1H); 2.40 (s, 3H); 2.21 (s, 6H); 2.01 and 1.99 (2s, 6H)

EXAMPLE 8A

4-Methyl-2-oxo-2H-1-benzopyran-7-yl 2-O-[(dimethylamino)acetyl]-3,4-di-O-acetyl-5-thio-β-D-xylopyranoside methanesulfonate The compound of EXAMPLE 8A is prepared by the same procedure as that of EXAMPLE 7A. (Yield=76%)

M.p.=110° C.; $[\alpha]_D^{23}$=−44° (c=0.29, CHCl$_3$)

EXAMPLE 9

4-Methyl-2-oxo-2H-1-benzopyran-7-yl 2,3-bis-O-[(dimethylamino)acetyl]-4-O-(2,2-dimethylpropanoyl)-5-thio-β-D-xylopyranoside dimethanesulfonate 2 g of compound II.4 are dissolved in 50 ml of dichloromethane in the presence of a 4 Å molecular sieve. 3 g of EDCI, 0.6 g of DMAP and 1.63 g of N,N-dimethylglycine are added. After stirring for 4 hours, the reaction mixture is filtered. The filtrate is washed with ammonium chloride solution and with water and is then dried over magnesium sulfate. The solvents are evaporated off under reduced pressure. The residue obtained is purified by chromatography on silica gel (eluent: dichloromethane/methanol, 10/1, v/v). 2.45 g of the compound obtained are dissolved in 50 ml of anhydrous ethyl acetate, and a solution of 600 µl of methanesulfonic acid in 13 ml of THF is then added dropwise. After stirring for 45 minutes, the precipitate is filtered off and dried. (Yield=69%)

M.p.=236° C.; $[\alpha]_D^{26}$=−19° (c=0.41, DMSO)

EXAMPLE 10

4-Methyl-2-oxo-2H-1-benzopyran-7-yl 4-O-acetyl-2,3-bis-O-[(dimethylamino)-acetyl]-5-thio-β-D-xylopyranoside dimethanesulfonate A solution of 500 mg of compound II.5 in 20 ml of dichloromethane is stirred under an inert atmosphere for 3 hours in the presence of 838 mg of EDCI, 167 mg of DMAP and 450 mg of N,N-dimethylglycine. The reaction mixture is then washed with water and the organic phase is concentrated under reduced pressure. The residue is purified by chromatography on silica gel using a dichloromethane/methanol mixture, 10/1, v/v, as the eluent. 490 mg of the compound obtained are taken up in 10 ml of ethyl acetate, and 135 µl of methanesulfonic acid in 2 ml of tetrahydrofuran are added. The precipitate is filtered off and dried under reduced pressure. (Yield=50%)

M.p.=130° C.; $[\alpha]_D^{22}$=−14° (c=0.39, DMSO)

EXAMPLE 11

4-Methyl-2-oxo-2H-1-benzopyran-7-yl 2,3,4-tri-O-(aminoacetyl)-5-thio-β-D-xylopyranoside tris (trifluoroacetate)

a) 4-Methyl-2-oxo-2H-1-benzopyran-7-yl 2,3,4-tri-O-[(N-tert-butoxycarbonylamino)acetyl]-5-thio-β-D-xylopyranoside, compound I'.1

A suspension of 325 mg of compound II.1 in 15 ml of dimethylformamide is heated until the solid has dissolved, and then cooled to room temperature. 578 mg of N-tert-butoxycarbonylglycine, 690 mg of 1-(3-dimethylaminopropyl)-3-ethylcarbodiimide hydrochloride and 184 mg of dimethylaminopyridine are added, with stirring. The reaction mixture is kept under these conditions for 20 hours and the dimethylformamide is then evaporated off under reduced pressure. The residue is taken up in dichloromethane. This organic phase is washed successively with 1N aqueous hydrochloric acid solution, sodium hydrogencarbonate solution and saturated sodium chloride solution and then dried over magnesium sulfate. The solvents in the organic phase are evaporated off under reduced pressure and the residue is then purified by chromatography on silica gel (toluene/ethyl acetate, 7/3, v/v). (Yield=80%)

$^1$H NMR (300 MHz, DMSO): 7.73 (d, 1H); 7.16 (m, 4H); 7.00 (dd, 1H); 6.29 (s, 1H); 6.00 (d, 1H, J=8.8 Hz); 5.40 (t, 1H); 5.30 (t, 1H); 5.07 (m, 1H); 3.68 (dd, 2H); 3.11 (t, 1H); 2.94 (dd, 1H); 1.38 (s, 9H)

b) 630 mg of compound I'.1 are dissolved in 75 ml of trifluoroacetic acid (TFA) and 25 ml of dichloromethane stabilized with amylene. The mixture is stirred at room temperature for 1 hour and the solvents are then evaporated off under reduced pressure. The residue is precipitated in diethyl ether and filtered off. This precipitate is then purified by chromatography on silica gel (water/acetonitrile/TFA, 4/1/0.001, v/v/v). The fraction containing the deprotected amine is lyophilized twice. (Yield=32%)

M.p.=136° C.; $[\alpha]_D^{24}$=−18° (c=0.155, CH$_3$OH)

EXAMPLE 11A

4-Methyl-2-oxo-2H-1-benzopyran-7-yl 2,3,4-tri-O-(aminoacetyl)-5-thio-β-D-xylopyranoside trihydrochloride 40 ml of a 1 M solution of hydrogen chloride in diethyl ether are added under an argon atmosphere at room temperature to a solution of 883 mg of compound I'.1 in 5 ml of anhydrous ethanol. After stirring for 18 hours, the white precipitate obtained is filtered off and then rinsed with anhydrous diethyl ether.

M.p.=180° C.; $[\alpha]_D^{26}$=−25° (c=0.42, CH$_3$OH)

EXAMPLE 12

4-Methyl-2-oxo-2H-1-benzopyran-7-yl 2,3,4-tri-O-[(methylamino)acetyl]-5-thio-β-D-xylopyranoside trihydrochloride The compound of EXAMPLE 12 is prepared from the compound II.1 and N-(tert-butoxycarbonyl)-N- methylglycine by a procedure analogous to that of EXAMPLES 11 and 11A.

M.p.=195° C.; $[\alpha]_D^{23}$=−26° (c=0.36, CH$_3$OH)

What is claimed is:

1. Compounds of formula (I):

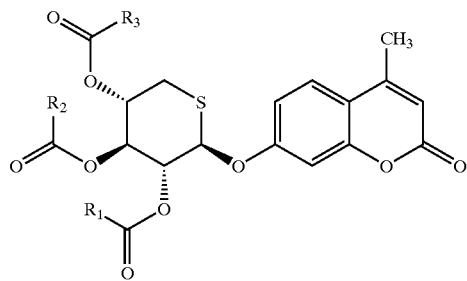

in which:

R$_1$, R$_2$ and R$_3$, are each independently:
- a (C$_1$–C$_6$)alkyl group,
- a pyridinyl group or
- a group —CH$_2$—NR$_4$R$_5$, in which R$_4$ and R$_5$ are each independently a hydrogen atom or a (C$_1$–C$_4$)alkyl group, or alternatively R$_4$ and R$_5$ form, with the nitrogen atom to which they are bonded, a pyrrolidinyl, piperidinyl, hexahydroazepinyl, morpholinyl or piperazinyl group, with the proviso that at least one of the substituents R$_1$, R$_2$ and R$_3$ is other than a (C$_1$–C$_6$)alkyl group, and their salts, solvates and hydrates, which are pharmaceutically acceptable.

2. Compounds according to claim 1, wherein R$_1$, R$_2$ and R$_3$ are each independently:
- a (C$_1$–C$_4$)alkyl group,
- a pyridin-3-yl group or
- a group —CH$_2$—NR$_4$R$_5$ in which R$_4$ and R$_5$ are each independently a hydrogen atom or a (C$_1$–C$_4$)alkyl group, or alternatively R$_4$ and R$_5$ form, with the nitrogen atom to which they are bonded, a pyrrolidinyl, piperidinyl or morpholinyl group, with the proviso that at least one of the substituents R$_1$, R$_2$ and R$_3$ is other than a (C$_1$–C$_4$)alkyl group.

3. Compounds according to claim 1, wherein at least two of the substituents R$_1$, R$_2$ and R$_3$ are identical.

4. Compounds according to claim 3, wherein R$_1$, R$_2$ and R$_3$ are identical and are selected from the group consisting of pyridinyl and a CH$_2$—NR$_4$R$_5$ group, in which R$_4$ and R$_5$ are each independently a hydrogen atom or a (C$_1$–C$_4$)alkyl group, or alternatively R$_4$ and R$_5$ form, with the nitrogen atom to which they are bonded, a pyrrolidinyl, piperidinyl, hexahydroazepinyl, morpholinyl or piperazinyl group.

5. Method for the treatment of thrombosis, comprising administration of a therapeutically effective amount of a compound which is an antithrombotic agent, wherein said compound is a compound of formula (I):

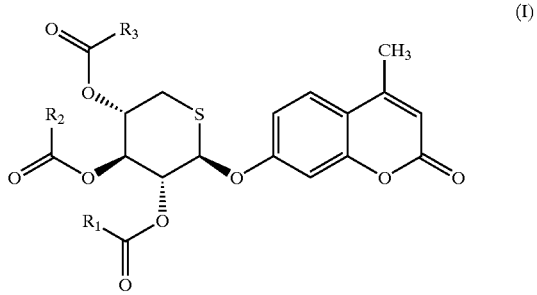

in which:

R$_1$, R$_2$ and R$_3$, are each independently:
- a (C$_1$–C$_6$)alkyl group,
- a pyridinyl group or
- a group —CH$_2$—NR$_4$R$_5$, in which R$_4$ and R$_5$ are each independently a hydrogen atom or a (C$_1$–C$_4$)alkyl group, or alternatively R$_4$ and R$_5$ form, with the nitrogen atom to which they are bonded, a pyrrolidinyl, piperidinyl, hexahydroazepinyl, morpholinyl or piperazinyl group, which the proviso that at least one of the substituents R$_1$, R$_2$ and R$_3$ is other than a (C$_1$–C$_6$)alkyl group, and their salts, solvates and hydrates, which are pharmaceutically acceptable.

6. Pharmaceutical compositions in which a compound according to claim 1 is present as the active principle, in association with a pharmaceutically acceptable excipient.

7. Pharmaceutical compositions according to claim 6 which are in injectable form.

* * * * *